United States Patent [19]
Ortiz

[11] Patent Number: 5,376,095
[45] Date of Patent: Dec. 27, 1994

[54] ENDOSCOPIC MULTI-FIRE FLAT STAPLER WITH LOW PROFILE

[75] Inventor: Mark S. Ortiz, Milford, Ohio

[73] Assignee: Ethicon Endo-Surgery, Cincinnati, Ohio

[21] Appl. No.: 148,036

[22] Filed: Nov. 4, 1993

[51] Int. Cl.⁵ ............................................. A61B 17/04
[52] U.S. Cl. ................................... 606/143; 227/175; 227/176; 227/179; 227/181
[58] Field of Search ..................... 606/219, 220, 143; 227/175, 176, 177, 19, 180, 175, 176, 179, 181

[56] References Cited

U.S. PATENT DOCUMENTS

| | | | |
|---|---|---|---|
| B1 5,040,715 | 4/1994 | Green et al. | 227/176 |
| 4,520,817 | 6/1985 | Green | 227/19 |
| 4,633,874 | 10/1987 | Chow et al. | 227/19 |
| 4,784,137 | 11/1988 | Kulik et al. | 227/19 |
| 5,040,715 | 8/1991 | Green et al. | 227/176 |
| 5,161,725 | 11/1992 | Murray et al. | 227/182 |
| 5,170,925 | 12/1992 | Madden et al. | 227/175 |

*Primary Examiner*—Stephen C. Pellegrino
*Assistant Examiner*—Gary Jackson
*Attorney, Agent, or Firm*—Matthew S. Goodwin

[57] ABSTRACT

A multi-fire endoscopic stapler is disclosed. The stapler has a retractable cartridge where the cartridge is retractable from a staple-forming position in which the distal-most staple in the cartridge is aligned with a driver blade on a staple driver for forming the staple against an anvil. An elongated shaft communicates with the anvil and driver, and means exist for forming the staple from the proximal end of the shaft, and for sequentially advancing each staple in the cartridge to the distal end of the cartridge. The retractable nature of the cartridge creates the ability to provide the stapler with a flat, low-profile, by eliminating the conventional stacked configuration of the anvil, driver, and staple cartridge. The stapler may be inserted through a small diameter opening frequently found during minimally invasive endoscopic surgical procedures, and then manipulated to sequentially form numerous staples against the anvil, one staple at a time, until the desired number of staples are fired.

6 Claims, 5 Drawing Sheets

ENDOSCOPIC MULTI-FIRE FLAT STAPLER WITH LOW PROFILE

BACKGROUND OF THE INVENTION

This invention relates specifically to an endoscopic surgical stapler having a generally flat configuration with a low profile especially adapted for insertion through a trocar cannula during minimally invasive surgical procedures.

Endoscopic surgery has recently exploded on the surgical scene. Endoscopy represents a form of minimally invasive surgery where surgery is performed through small diameter openings made through the body wall providing access to the surgical site. These openings are now typically made with a trocar, which is a puncturing device for gaining such access. Once the cutting tip of the trocar has penetrated the body wall, the cutting implement is removed from the trocar, leaving behind the trocar cannula, which is a tubular sheath, for providing a pathway into the body for required endoscopic instrumentation and surgical instruments.

Endoscopic surgery represents a significant advance in the state of surgical practice because overall trauma to the patient is significantly decreased, healing times are shortened, and hospital costs are dramatically reduced. While the explosion in endoscopic surgical techniques continues, it has created an ever pressing need for surgical instruments to keep pace with the innovative procedural advances which minimally invasive surgery can bring.

Recent advances have been made in the design and operation of surgical staplers for their adaptation to endoscopic surgery. Surgical staplers fire staples to fasten bodily tissue during surgery, and have become a viable alternative to traditional suturing techniques for fastening because of the relative ease in which the staples can be placed. An example of an endoscopic stapler can be found in U.S. Pat. No. 5,170,925, which describes an endoscopic stapler for remotely laying two double parallel rows of staples. The ability to remotely fire the stapler to place the staples is critical for endoscopic applications, since it is necessary to fire the stapler through the small diameter trocar cannula, unlike open surgical procedures where the surgeon has direct access to the surgical site. The stapler described in this patent is housed within a tubular sheath configured to fit through the cannula of the surgical trocar, and the stapling functions can be accomplished remotely from the anvil and firing mechanisms. The rows of staples are placed along the longitudinal axis of the sheath, and a knife can be actuated to cut between the center two rows of staples. This type of stapler is now routinely used during endoscopic bowel surgery. Unfortunately, it is incapable of placing staples transversely to the longitudinal axis of its tubular sheath, which is an important consideration for certain surgical procedures.

The importance of being able to fire staples transversely to the longitudinal axis of the housing or shaft of the stapler should not be underestimated. The transverse placement of staples is important for numerous surgical techniques, especially for a procedure referred to as an "esophageal reflux procedure". Gastro-esophageal reflux, or "GER", can be a major problem with profound consequences for both children and adults. Symptoms of GER commonly include reflux or regurgitation of the stomach contents up into the esophagus. Although numerous "anti-reflux" procedures now are beginning to be developed, all of them require the use of surgical staples for fastening. In particular, an endoscopic surgical stapler would be particularly desired for this application, especially one which sequentially fires numerous staples, one staple at a time, in a direction which is transverse to the longitudinal axis of the stapler shaft. Ideally, this stapler would also have the ability to compress the tissue before the staples are fired.

Staplers currently do exist which fire staples transversely to the longitudinal axis of the stapler shaft or housing. See, for example, U.S. Pat. No. 5,161,725, which describes a rotating head skin stapler for approximating skin tissue. This stapler fires staples transversely relative to the longitudinal axis of the stapler housing and its rotating head. Unfortunately, the stapler housing has a very large profile, and therefore would not be conducive for endoscopic surgery because it would be impossible to insert the stapler through a small diameter endoscopic opening. In addition, it is incapable of compressing the tissue prior to firing. Another example of such a stapler is the Brookstone Staoler (marketed by Brookstone), which is a non-surgical stapler having a low, flat profile when the stapler is not being fired. Its flat profile can be obtained because the cartridge can be retracted from its staple-forming position. The staples are fired transversely relative to the longitudinal axis of the stapler shaft. Once again, however, this stapler is not adapted for endoscopic use because of the user's inability to actuate the driving and staple-forming mechanisms of the stapler from a position remote from these mechanisms themselves.

In view of the deficiencies inherent with the prior art staplers, what is needed is a multi-fire endoscopic stapler which has a flat, low profile to facilitate its use during minimally invasive endoscopic surgical procedures. Such a stapler would have the ability not only to fire staples transversely relative to the longitudinal axis of its shaft, but also compress tissue within its jaws prior to firing of the staples. The desired stapler would be capable of sequentially firing numerous staples, one staple at a time. In addition, it is critical for the proper operation of such an endoscopic stapler to have the ability to form each staple from a position remote from the staple-forming mechanism.

SUMMARY OF THE INVENTION

The invention is a multi-fire endoscopic stapler. The stapler comprises a staple-forming anvil, a staple driver which has a driver blade for forming a staple against the anvil, an elongated shaft communicating with the anvil and driver, and means for forming the staple from the proximal end of the shaft. It also comprises a cartridge containing a plurality of staples displayed between the anvil and driver. Significantly, the cartridge is retractable from its staple-forming position. In its staple-forming position, the distal-most staple in the cartridge is aligned with the driver blade on the staple driver for forming the staple against the anvil. Lastly, the stapler comprises means for sequentially advancing each staple in the cartridge to the distal end of the cartridge.

The preferred stapler fires each staple transversely to the longitudinal axis of the staple-forming anvil. Additionally, the staple driver of the preferred stapler is pivotally attached to the anvil for pivoting movement of the driver from an open position to a closed position. The cartridge is retractable from the staple-forming position to a retracted position. In its retracted position, the cartridge is seated proximally of the driver blade when the driver is in its closed position. When the cartridge is retracted and the driver closed, the driver blade of the driver is adjacent to the anvil, and the anvil and driver are substantially parallel to each other.

In an especially preferred embodiment of this invention, the stapler includes means for remotely retracting the cartridge from the staple-forming position to the retracted position, and means for remotely pivoting the driver from the open position to the closed position, from the proximal end of the shaft. These capabilities for remotely retracting the cartridge and pivoting the driver are particularly desired to facilitate efficient use of the stapler during endoscopic surgery where access to the surgical site is restricted to the passageways made possible from small diameter trocar cannulas.

The preferred endoscopic stapler of this invention can sequentially fire numerous staples, one staple at a time, transversely to the longitudinal axis of the staple-forming anvil, during endoscopic surgery. Additionally, it can compress tissue between the anvil and driver prior to firing the staples. But most importantly, the stapler has a flat, low profile which is especially desired during minimally invasive endoscopic surgical procedures. The key to this flat profile, which is represented by the height of the stapler when the driver is in its closed position, is that the anvil, staple cartridge, and driver do not need to enter the body "stacked-up". This is possible because the cartridge can retract from its startle-forming position to a retracted or "over-bite" position, where the driver blade on the driver is located distally of the staple cartridge and in close proximity with the anvil. When the stapler is inserted into the patient and the driver is pivoted to its open position, the cartridge can be advanced forward so that the distal-most staple is displayed between, and aligned with, the driver blade of the driver and the anvil. When this distal-most staple is formed against the anvil, the next staple is positioned in alignment with the driver blade for subsequent placement. In this manner, additional staples, as desired, can be formed against the anvil for the fastening of the intended bodily tissue. Subsequently, when stapling is complete, the cartridge can be retracted, the driver pivoted to the closed position, and the compacted, low-profile stapler can now be readily removed from the small diameter opening. Therefore, the ability to retract the cartridge and create the "over-bite" configuration can eliminate the height of the staple legs inside the cartridge from the overall height of the stapler. In this way, a flat profile is obtained.

The stapler of this invention is useful during any endoscopic procedure where it is desirable to sequentially fire numerous staples, one at a time, especially when it is desired to fire each staple transversely to the longitudinal axis of the staple-forming anvil. Furthermore, the benefits of this stapler may best be realized when in addition to the desire to sequentially fire staples transversely to the longitudinal axis of the anvil, it is also desired to hold together two layers of bodily tissue between the anvil and driver for compression prior to firing. One procedure where these characteristics are especially needed is the esophageal reflux procedure, although it can readily be envisioned that the stapler of this invention can be used in other surgical procedures.

BRIEF DESCRIPTION OF THE DRAWINGS

An embodiment of the invention is described by way of example with reference to the accompanying drawings, in which.

DETAILED DESCRIPTION OF THE PREFERRED EMBODIMENT

Figure 1:
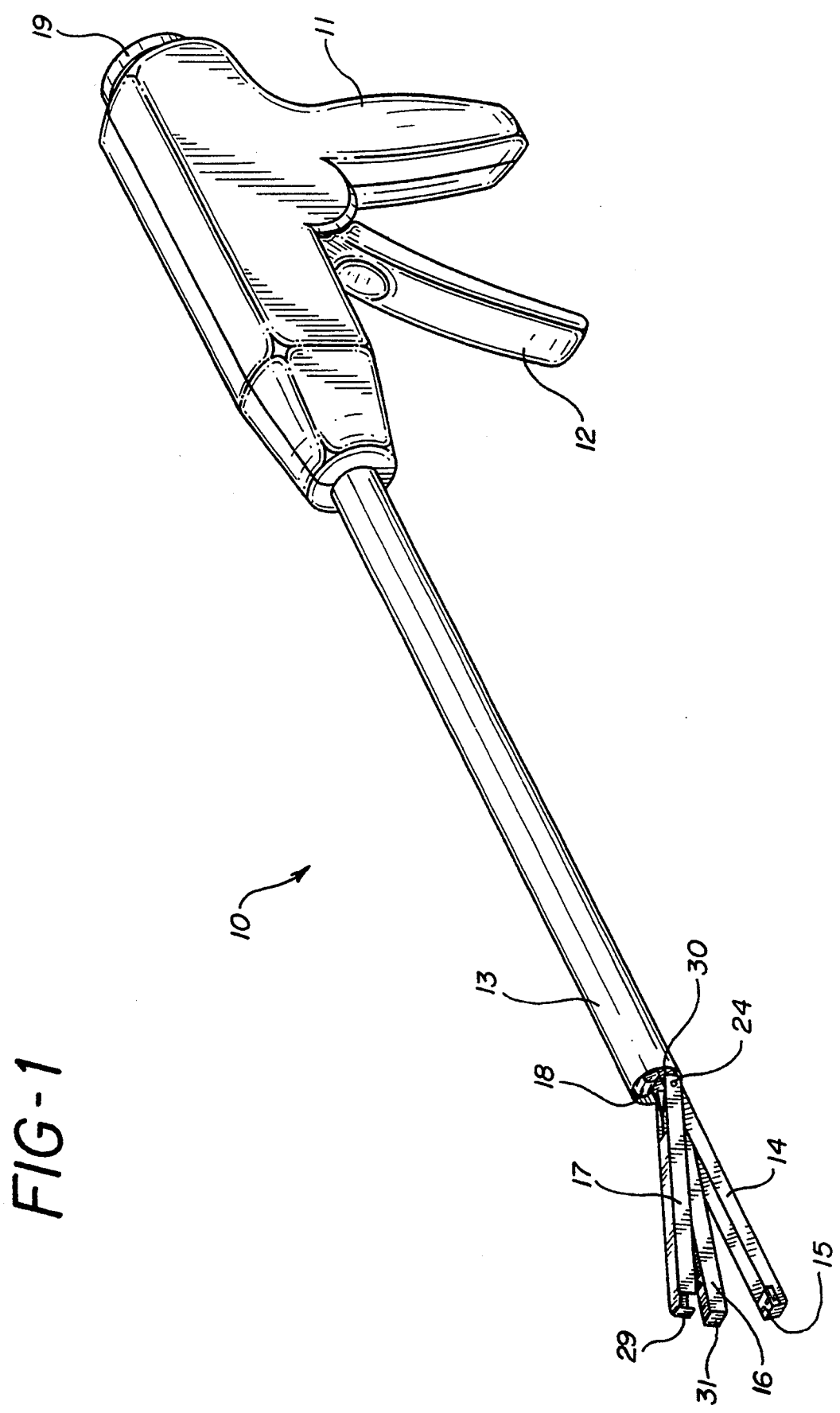
FIG. 1 is a perspective view of the endoscopic stapler in its open position.
Figure 2:
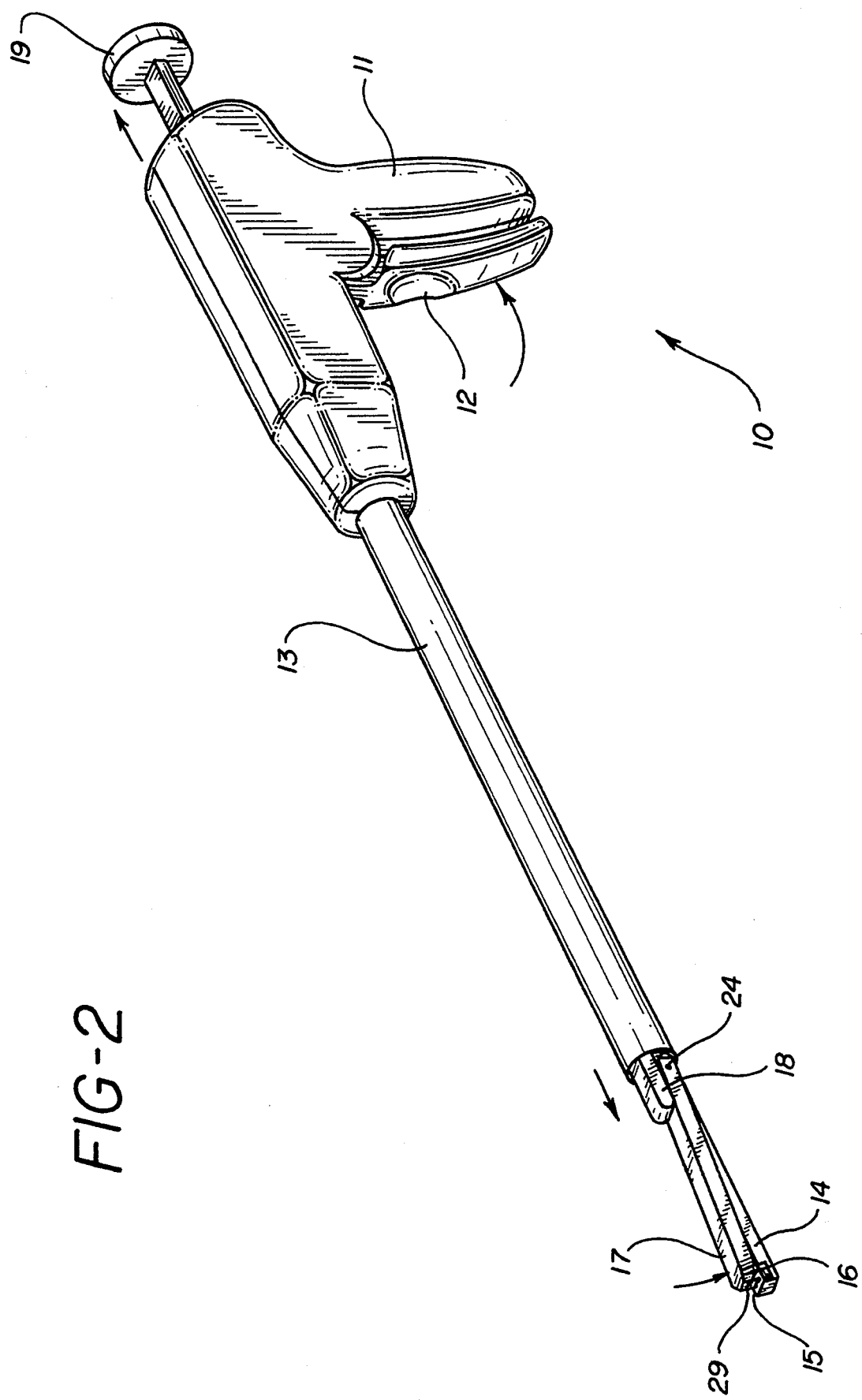
FIG. 2 is a perspective view of the endoscopic stapler in its closed position.

Referring now to FIG. 1, there is shown the preferred endoscopic multifire flat stapler 10. It has a handle 11, and a trigger 12, pivotable towards the handle. Extending from the handle is shaft 13, and at the distal end of the shaft are connected a base 14, cartridge 16 and driver 17. When the endoscopic flat stapler 10 is inserted through a small opening, such as a trocar cannula, the base, cartridge and driver must be stacked in a geometrical relationship which will produce the smallest cross-sectional area. In this low-profile arrangement, the cartridge is sandwiched between the driver and the base, and the driver and base are positioned substantially parallel to each other.

The creation of the stacked relationship of the base, cartridge and driver is depicted in FIGS. 1, 2, 4 and 5. The user of the stapler first pulls the cartridge control rod 19 to its proximal extended position. This pulling motion causes the cartridge cable 25 (FIG. 4), which is attached at its proximal end to the control rod 19 and at its distal end to the cartridge 16, to pull the cartridge to its retracted position as shown most clearly at FIGS. 2 and 5. The retraction of the cartridge 16 is made possible in part by slot 35 in the cartridge, which allows the cartridge to reciprocate axially. The retraction of the cartridge is resisted by cartridge return spring 27.

After the cartridge 16 is retracted, trigger 12 is then squeezed toward handle 11 (FIG. 2) causing an arcing motion of the trigger around trigger pin 22 (FIG. 3), which in turn causes axial force to be applied through pin 23 moving in slot 36. The resulting force causes forward or distal motion to wedge rod 18. This distal motion of wedge rod 18 causes the rod to contact driver 17 causing arcing motion to the driver pivoting around driver pin 24 (FIG. 4). The driver is therefore urged toward the cartridge 16 and base 14. The driver 17 is constructed to allow interior space to enclose the cartridge 16 when the cartridge is in its retracted position. In other words, the retracted cartridge can fit entirely within the outer walls of the driver 17. The arcing motion of the driver caused by distal motion of wedge rod 18 is stopped by the driver blade 29 coming in contact with staple forming anvil 15 attached to stapler base 14, as shown at FIGS. 4 and 5. When the cartridge is retracted, and the driver urged against the anvil 15 on base 14, the cartridge seats within driver 17 in the "over-bite" position where the driver blade 29 is positioned adjacent to the distal end of the cartridge. Thus, the driver 17 and base 14 are positioned substantially parallel to each other, and the low-profile arrangement of the business end of the stapler is obtained.

Figure 3:
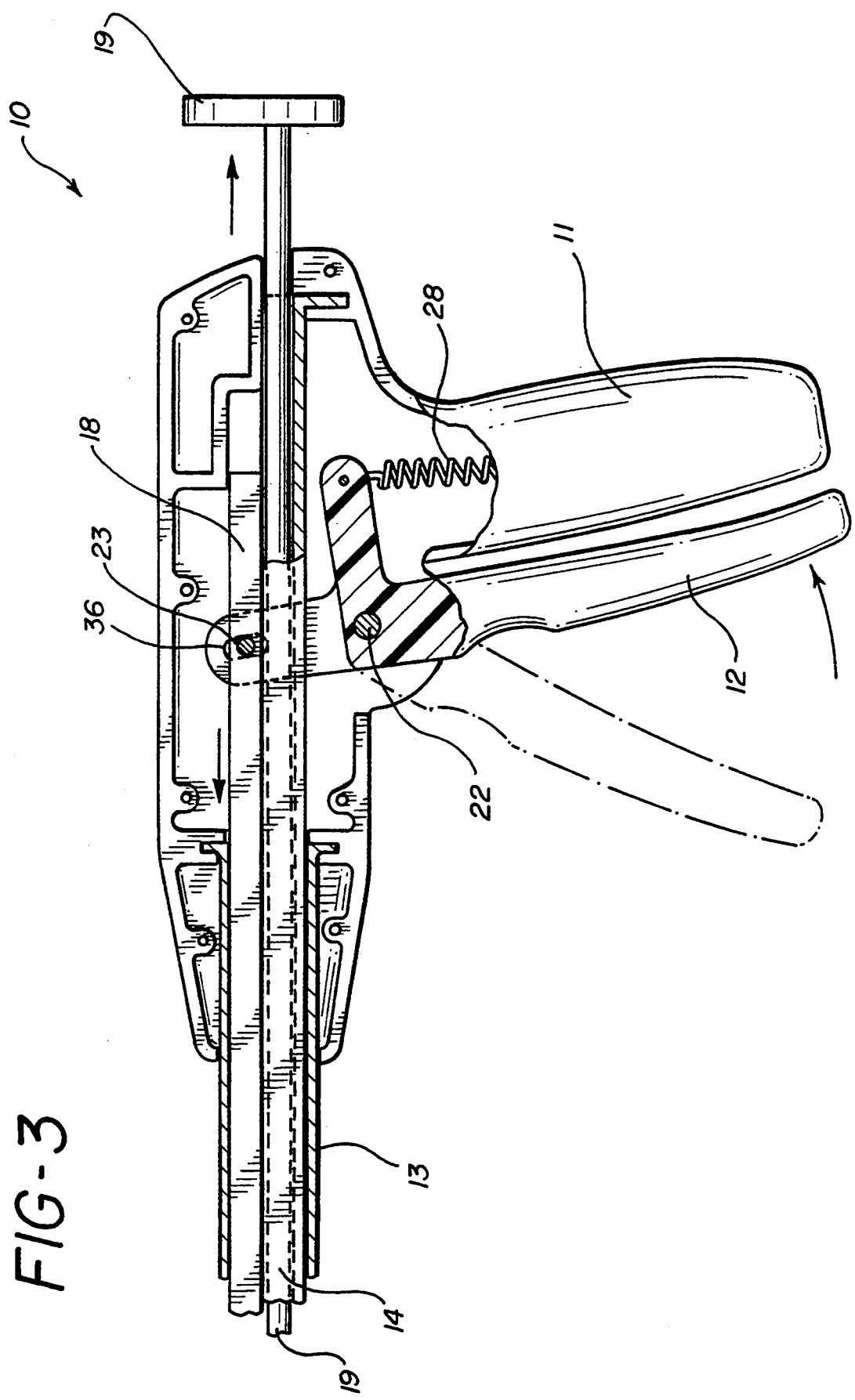
FIG. 3 is a partial section of the proximal handle portion of the stapler.
Figure 4:
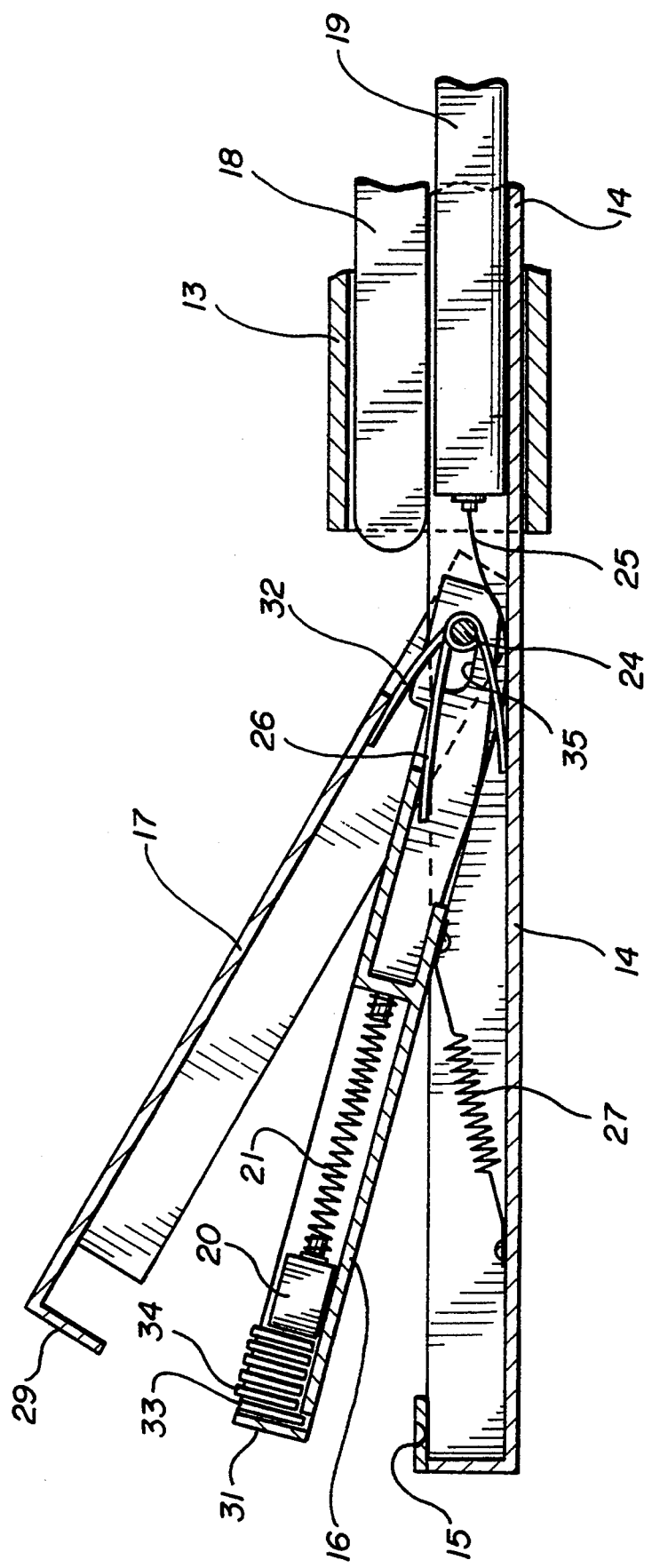
FIG. 4 is a partial section of the distal end of the stapler in its firing position.
Figure 5:
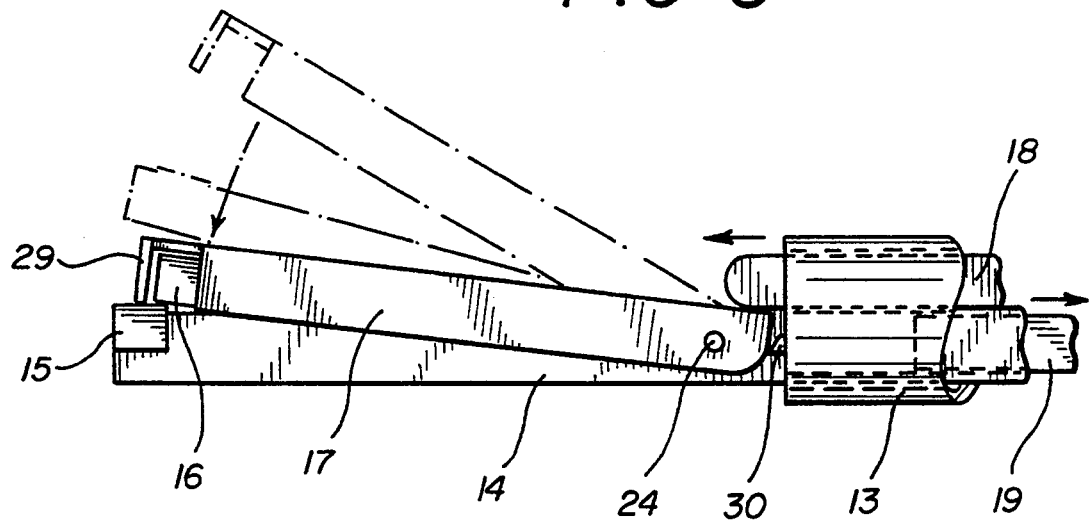
FIG. 5 is a right side view of the distal end of the stapler in its closed position.

Once the flat stapler is inserted through a trocar cannula, it is made ready for use, as shown in FIGS. 1, 3 and 4, by first releasing the trigger 12. This allows the handle return spring 28 to cause the trigger to move away from handle 11 in an arcing motion around trigger pin 22. This in turn causes rod 18 to move proximally through the spring force transmitted by pin 23. When the wedge rod 18 moves proximally, the wedge rod will lose contact with driver 17 allowing the driver to move away from base 14 in an arcing motion through force provided by driver return spring 32. The driver 17 motion is limited by stop 30 on base 14, as shown in FIG. 5. Simultaneously with the driver motion, cartridge 16 follows driver 17 in a similar arcing motion centered around pin 24. The cartridge motion is caused by cartridge spring 26. Cartridge 16 arcing travel ceases when the cartridge contacts driver 17.

Figure 6:
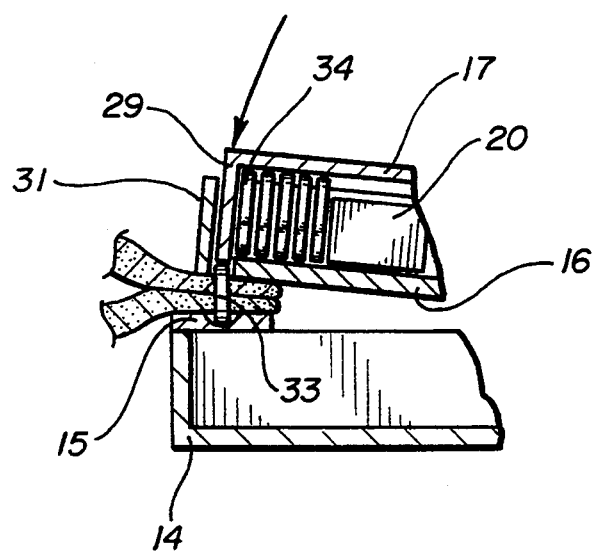
FIG. 6 is a partial section of the distal end of the stapler showing a staple being formed through two layers of tissue.

The stapler 10 is ready for use in stapling tissue when cartridge control rod 19 is moved distally to allow cartridge 16 to move distally from its retracted position to its firing position. Cartridge 16 moves distally from force provided by cartridge return spring 27. In the firing position, driver blade 29 is located directly above staple 33 which in turn is directly above the transverse centerline of anvil 15, as shown in FIG. 6.

Stapler 10 is positioned with the layers of tissue to be fastened placed between cartridge 16 and base 14. Trigger 12 is squeezed causing wedge 18 to move distally using force transmitted through wedge pin 23. The distal motion of wedge 18 causes contact between the wedge and driver 17 causing arcing motion of driver blade 29 toward staple 33 and anvil 15. The driver blade contacts staple 33 resting against block 31 of cartridge 16, forcing staple 33 downward through the tissue layers to be fastened, and into anvil 15 causing staple 33 to form an approximate "B" shape when the arcing motion of driver blade 29 is completed. FIG. 6 shows the tissue stapling in progress.

After staple 33 is formed, trigger 12 is released causing wedge 18 to move proximally. With trigger 12 in its extended position, wedge 18 is not in contact with driver 17, allowing driver 17 and cartridge 16 to return to their open positions by force from driver spring 32 and cartridge spring 26. The formed staple remains in the tissue and is replaced by adjacent staple 34 from the plurality of staples in the cartridge. The adjacent staple in the cartridge is forced distally to the distal end of the cartridge by the feed spring 21 pushing on feed block 20. When this staple is now positioned at the distal end of the cartridge, it is then properly aligned with the driver blade for forming against the anvil. The forming sequence can be repeated until the last staple is formed, at which time the stapler is deactivated by feed block 20. This block invades the space normally occupied by staple 33, and therefore stops the travel of driver 29.

This invention has been described with respect to its most preferred embodiment. However, the reader should realize that numerous additional embodiments are contemplated within the scope of this invention as it is defined by the appended claims.

What is claimed is:

1. A multi-fire endoscopic stapler comprising:
   a) a staple-forming anvil;
   b) a staple driver pivotally attached to said anvil for pivotal movement from an open position to a closed position, said driver having a driver blade thereon for sequentially forming a plurality of staples against said anvil;
   c) an elongated shaft in alignment with said anvil and driver;
   d) means in alignment with said driver for forming said staple from the proximal end of said shaft;
   e) a cartridge containing said staples disposed between said anvil and driver, said cartridge retractable in relation to said anvil and driver from a staple-forming position wherein a distal-most staple in said cartridge is aligned with said driver blade for forming said distal-most staple against said anvil; and
   f) means interposed between said anvil and said driver for sequentially advancing said staples to the distal end of said cartridge.

2. The stapler of claim 1 wherein said staples are sequentially formed transverse to the longitudinal axis of said anvil.

3. The stapler of claim 2 wherein said cartridge is retractable in relation to said anvil and driver from said staple-forming position to a retracted position wherein said cartridge is seated proximally of said driver blade when said driver is in said closed position.

4. The stapler of claim 3 wherein said driver blade of said driver is adjacent to said anvil, and said anvil and driver are substantially parallel to each other, when said cartridge is in said retracted position and said driver is in said closed position.

5. The stapler of claim 4 wherein said stapler further comprises means movable within said shaft for retracting said cartridge from said staple-forming position to said retracted position from the proximal end of said shaft.

6. The stapler of claim 5 wherein said stapler further comprises means movable within said shaft for pivoting said driver from said open position to said closed position from the proximal end of said shaft.

* * * * *